United States Patent [19]

Adams

[11] Patent Number: 5,385,575
[45] Date of Patent: Jan. 31, 1995

[54] IMPLANTABLE CARDIOVERTER DEFIBRILLATOR HAVING VARIABLE OUTPUT CAPACITANCE

[75] Inventor: Theodore P. Adams, Edina, Minn.

[73] Assignee: Angeion Corporation, Plymouth, Minn.

[21] Appl. No.: 128,859

[22] Filed: Sep. 29, 1993

Related U.S. Application Data

[63] Continuation-in-part of Ser. No. 856,982, Mar. 24, 1992, abandoned, and a continuation-in-part of Ser. No. 999,393, Dec. 31, 1992.

[51] Int. Cl.$^6$ ............................................. A61N 1/39
[52] U.S. Cl. ........................................ 607/5; 607/15
[58] Field of Search ............................ 607/5, 6, 7, 15

[56] References Cited

U.S. PATENT DOCUMENTS

| | | |
|---|---|---|
| 3,093,136 | 6/1963 | Lohr . |
| 3,924,641 | 12/1975 | Weiss . |
| 4,708,145 | 11/1987 | Tacker, Jr. et al. . |
| 4,727,877 | 3/1988 | Kallok . |
| 4,850,357 | 7/1989 | Bach, Jr. . |
| 4,953,551 | 9/1990 | Mehra et al. . |
| 5,083,562 | 1/1992 | de Coriolis et al. . |
| 5,107,834 | 4/1992 | Idecker et al. . |
| 5,199,429 | 4/1993 | Kroll et al. . |

FOREIGN PATENT DOCUMENTS

| | | |
|---|---|---|
| 0272021 | 7/1964 | Australia . |
| 0280526 | 8/1988 | European Pat. Off. . |

OTHER PUBLICATIONS

Medtronic ® PCT ™ Device Tachyarrhythmia Control System Reference Guide Apr. 1992.
Ventritex ® Cadence ® Tiered Therapy Defibrillator System Cadence Model V-100 and Cadence Programmer, Prel. Physician's Manual, Oct. 1990.
Ventak ® PRx ™ 1700/1705 Physician's Manual, Cardiac Pacemarks, Inc.

Primary Examiner—William E. Kamm
Assistant Examiner—Scott M. Getzow
Attorney, Agent, or Firm—Patterson & Keough

[57] ABSTRACT

An improved implantable cardioverter defibrillator (ICD) system having a programmable switched and variable range of effective output capacitance values for the purpose of producing a capacitive-discharge countershock. The improvement comprises a pulse generating capacitor arrangement for the ICD system that includes two or more separate capacitor systems and a system for selectively electrically connecting each of the capacitor systems in parallel with the other capacitor systems during the charging and discharging of the pulse-generating capacitor arrangement, such that the pulse generating capacitor arrangement has at least two different selectable effective output capacitance values. With this type of capacitor arrangement, it is possible to reduce the countershock energy in discrete steps as the duration of the countershock is decreased, while still preserving the value of the initial discharge voltage, and hence the conversion effectiveness. Reducing countershock pulse duration in steps having differing output capacitance also preserves the fraction of stored energy that is delivered to the heart, and hence, preserves the efficiency of the system, thereby conserving battery life, reducing ICD system size, or both.

12 Claims, 4 Drawing Sheets

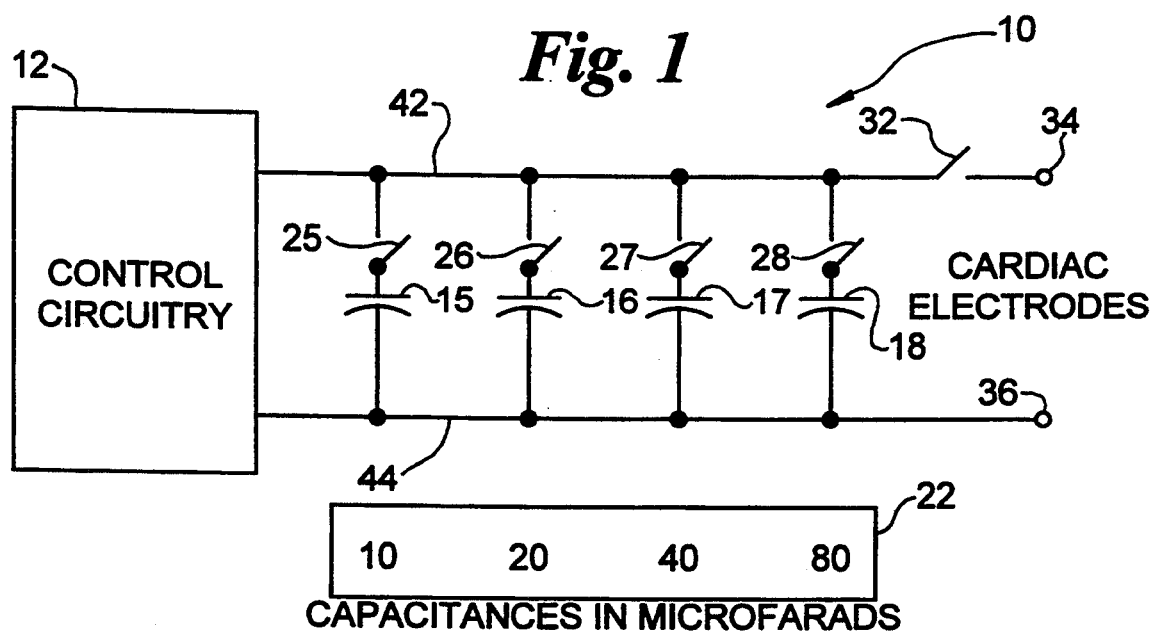
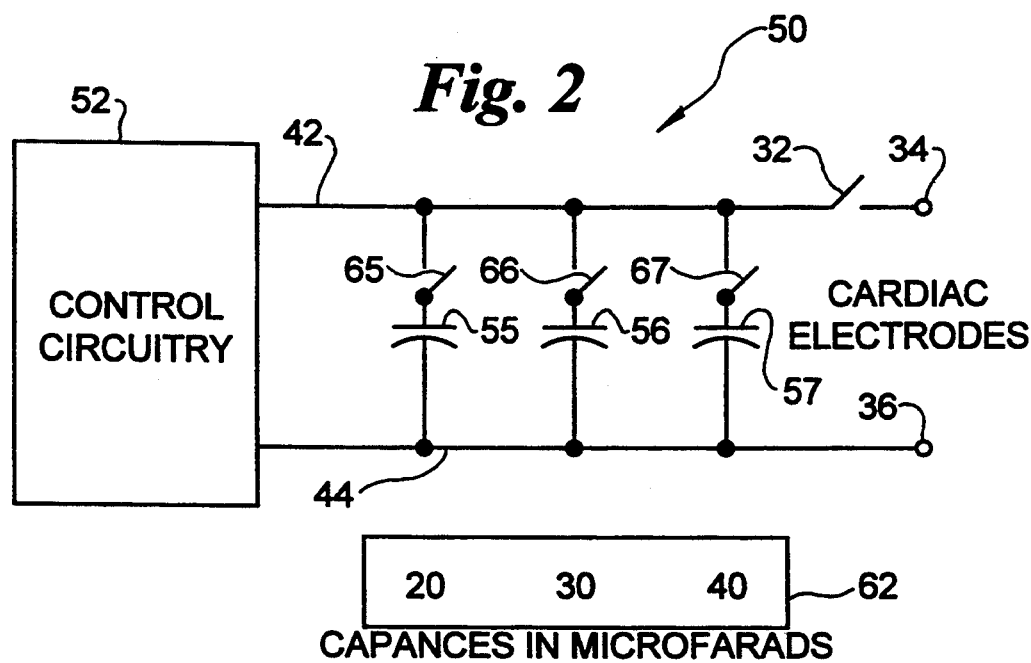

IMPLANTABLE CARDIOVERTER DEFIBRILLATOR HAVING VARIABLE OUTPUT CAPACITANCE

RELATED APPLICATIONS

This application is a continuation-in-part of two prior co-pending application, the first of which was filed in the United States Patent and Trademark Office on Mar. 24, 1992, and entitled SUCCESSIVE CHANGEABLE DEFIBRILLATION WAVEFORMS, Ser. No. 07/856,982, now abandoned the second of which was filed on Dec. 31, 1992, and entitled IMPLANTABLE DEFIBRILLATOR SYSTEM, Ser. No. 07/999,393, and both of which are assigned to the same assignee of the present invention and the disclosure of each of which is hereby incorporated in the present application. This patent application is also related to two co-pending applications filed in the United States Patent and Trademark Office, the first of which was filed on Feb. 18, 1992, and entitled OPTIMAL PULSE DEFIBRILLATOR, Ser. No. 07/835,836, and the second of which was filed on Apr. 9, 1992, and entitled SHORT PULSE CARDIOVERSION METHOD FOR IMPLANTABLE SYSTEMS, Ser. No. 07/866,460, both assigned to the same assignee as the present invention, and the disclosure of both of which is incorporated by reference in the present patent application.

BACKGROUND OF THE INVENTION

1. Field of the Invention

The present invention relates generally to implantable cardioversion-defibrillation (ICD) processes and systems, and more particularly to processes and systems that provide a programmable choice of a range of output capacitance values.

2. Description of the Background Art

Unlike existing external cardioversion-defibrillation systems which can deliver electrical countershocks of a wide variety of wave types and wave shapes from electronic circuitry that is located outside the human body, an implantable cardioversion-defibrillation (ICD) system must have electronic circuitry which is small enough to fit within an implantable device. This size limitations imposes significant constraints on the wave type and wave shape which can be delivered as an electrical countershock.

In all of the ICD systems available today, a truncated capacitive-discharge countershock is delivered by the implanted device to electrodes that are positioned in, on, or near the heart. To generate the truncated capacitive-discharge countershock, existing ICD systems use an internal battery system to charge a relatively small, but powerful, output capacitor system to a relatively high discharge voltage, the output of which is then discharged into the heart through the electrodes. After the output decays to a predetermined output voltage, or after a predetermined countershock duration has elapsed, the capacitive-discharge countershock is truncated and the remaining energy in the output capacitor system is dissipated within the ICD system. In existing ICD systems, the output wave shape of the countershock may be either a traditional monophasic waveform, or a biphasic waveform in which the polarity of the output discharge is reversed at some point during the discharge to present a second or reversed "phase".

In a given patient, there is a certain threshold energy required to achieve cardioversion, and usually a considerably higher value required to achieve defibrillation. Within the human population, these threshold values for countershocks delivered to implanted electrodes range widely, from approximately one joule to almost forty joules, depending upon such factors as the types and locations of the electrodes, the type of countershock, and the cardiac condition of the patient, for example. At the time an ICD system is implanted in a patient, the attending physician will empirically determine a minimum defibrillation threshold for the patient, and will program the charging voltages for the countershocks to be delivered as part of a therapy regimen within the range of maximum voltages allowed by the device.

Presently, there are three different ICD systems which have received device approval from the Federal Drug Administration, the PCD ® device, available from Medtronic, Inc., of Minneapolis, Minn., the Cadence ® device, available from Ventritex, Inc,. Mountain View, Calif., and the Ventak-P ® device, available from Cardiac Pacemakers, Inc., St. Paul, Minn. The existing ICD systems are all capable of delivering a maximum countershock of up to 700 to 750 volts having a total energy of between 31 to 44 joules. In each of these ICD systems, the capacitor system consists of a pair of identical electrolytic capacitors that are connected in series and charged by a split winding transformer with one secondary winding connected to a first of the capacitors and the other secondary winding connected to a second of the capacitors. This arrangement overcomes the charging voltage limitations of the electrolytic capacitors that would otherwise limit the maximum charging voltage of the electrolytic capacitors to about 375 volts. Each of the pair of capacitors has the same capacitance value in the range of 280–360 microfarads. Because the pair of capacitors are discharged in series, there is a single total effective output capacitance of the capacitor system that is the equivalent of the series combination of the individual capacitance value of each capacitor, in this case one-half of the capacitance value of each of the individual capacitors. Thus, each of the existing ICD systems has a set effective output capacitance value that is someplace between 140–180 microfarads, depending upon the capacitance value of the identical pair of electrolytic capacitors used to make up the capacitor system.

In a capacitive-discharge system, the total energy stored in the capacitor can be determined by the equation:

$$E_s = 0.5 \, CV^2 \qquad \text{Eq.(1)}$$

where C is the output capacitance of the ICD system and V is the initial discharge voltage of the countershock. The portion of the stored energy ($E_s$) that is actually delivered to the heart during a countershock can be determined by the equation:

$$E_d = E_s \, \text{tilt} \qquad \text{Eq.(2)}$$

where the tilt is a measure of the pulse duration of the truncated capacitive discharge usually expressed in terms of a percentage of the initial charging voltage ($V_i$) to the final truncated voltage ($V_f$) as defined by the equation:

$$\text{tilt} = (V_i - V_f)/V_i \qquad \text{Eq.(3)}$$

Alternatively, because the voltage decay of the capacitive discharge is a natural exponential decay, tilt may also be expressed directly as a function of the duration of the truncated capacitive discharge in terms of the equation:

$$\text{tilt} = V_i(1 - e^{-d/\tau}) \qquad \text{Eq.(4)}$$

where $\tau$ is the time constant of the ICD system as defined by the average resistance of the myocardium between the discharge electrodes (R) times the effective output capacitance of the ICD system (C).

It is generally accepted that achieving cardioversion or defibrillation with a countershock of the lowest possible energy brings benefits. One such benefit is that a lower energy delivered countershock minimizes patient hazard and discomfort during the countershock. Another benefit is that a lower energy delivered countershock may also lead to a decrease in the size of the battery and capacitor system required to deliver such a countershock, and, hence, to an ICD system having a smaller size, a longer life, or both. In addition, a capacitor system having a smaller effective capacitance reduces the energy drawn from the battery system in order to deliver the countershock, thereby resulting in a longer life for the battery system, a smaller size for the battery system, or a combination of both.

Because existing ICD systems have but one output capacitance value (C), the simplest and most customary way to reduce the energy ($E_d$) of the countershock is to reduce the initial discharge voltage ($V_i$), leaving the pulse duration of the countershock about the same. The problem which this technique engenders is that the effectiveness of both the cardioversion and defibrillation therapies are diminished by reducing the initial discharge voltage.

In the previously referenced co-pending applications entitled "Optimal Pulse Defibrillator", and "Short Pulse Cardioversion Method for Implantable Systems", it is disclosed that a higher percentage of successful conversions in both defibrillation and cardioversion can be achieved by preserving a high value for the initial discharge voltage, and, instead, diminishing the duration of the countershock pulse in order to reduce both the stored energy ($E_s$) and the delivered energy ($E_d$) of the countershock. A particularly favorable combination of initial voltage and pulse duration involves a value of the initial discharge voltage that falls between 500 and 800 volts, and a value of the countershock pulse duration that approximates the characteristic or chronaxie time of the heart and falls in the range from 1 to 4 milliseconds.

Thus, it is possible to achieve a higher success rate for cardioversion and defibrillation by truncating the capacitive discharge at an earlier point. The problem with this approach to reducing the energy of the countershock is that the ICD ends up wasting energy because there is more unused energy that remains in the capacitor system when it is truncated earlier. As a result, the energy delivered to the heart is now a smaller fraction of that initially stored in the capacitor system, and a larger fraction remains in the capacitor after discharge to be dissipated in the ICD system and thus wasted.

While the shorter pulse durations taught by the co-pending application may prove more successful with less output energy for the countershock, when shorter pulse durations are implemented in existing ICD systems the goal of reducing the overall energy requirements of the ICD system are not achieved due to the wasted energy that remains in the capacitor system after truncation. Consequently, it would be advantageous to provide an ICD system which can take advantage of the energy reductions afforded by shorter pulse duration cardioversion and defibrillation countershocks without wasting the energy that remains in the capacitor system after truncation of the capacitive-discharge countershock.

SUMMARY OF THE INVENTION

The present invention overcomes the effectiveness-versus-efficiency tradeoff incurred with a shorter duration countershock by providing an implantable cardioverter defibrillator (ICD) system having a programmable switched and variable range of effective output capacitance values for the purpose of producing a capacitive-discharge countershock. With this type of capacitor arrangement, it is possible to reduce the countershock energy in discrete steps as the duration of the countershock is decreased, while still preserving the value of the initial discharge voltage, and hence the conversion effectiveness. Reducing countershock pulse duration in steps having differing output capacitance also preserves the fraction of stored energy that is delivered to the heart, and hence, preserves the efficiency of the system, thereby conserving battery life, reducing ICD system size, or both.

In accordance with a first embodiment of the present invention, there is provided an improved ICD system for producing a capacitive-discharge countershock that has a programmable choice of output capacitance values. The ICD system is a self-contained human implantable device that includes a pulse-generating capacitor arrangement for storing an electrical charge of greater than 1 joule, a battery for internally charging the pulse-generating capacitor means, and control mechanisms for selectively discharging the electrical charge in the pulse-generating capacitor as a countershock to be delivered through electrodes implanted in a human patient in response to a sensing of a myocardial arrhythmia in the human patient. The improvement of the present invention comprises a pulse generating capacitor arrangement that includes two or more separate capacitor systems and a system for selectively electrically connecting each of the capacitor systems in parallel with the other capacitor systems during the charging and discharging of the pulse-generating capacitor arrangement, such that the pulse generating capacitor arrangement has at least two different selectable effective output capacitance values.

In another embodiment of the present invention, the control mechanism for selectively controlling the discharge of the electrical charge stored in the pulse-generating capacitor arrangement includes the choice to vary the output capacitance from one countershock to the next for a preprogrammed sequence of countershocks to be delivered as part of a multiple-countershock therapy regimen in response to a continued sensing of the myocardial arrhythmia. In this embodiment, the control mechanisms for selectively discharging the electrical charge including memory for storing selected control information to generate a preprogrammed sequence of countershocks to be delivered as part of the multiple-countershock therapy regimen. The selected control information includes a programmable initial charging voltage value and a programmable pulse duration value for each countershock and further includes a programmable effective output capacitance value for each countershock for controlling the system for selectively electrically connecting each of the capacitor systems.

One way of accomplishing the improved pulse-generating capacitor arrangement of the present invention is to provide a group of three or more separate capacitors that can be electrically connected in parallel, each capacitor having a switch in series with on output terminal of that capacitor so that the capacitor can be included in, or excluded from, the parallel combination of the capacitors in the pulse-generating capacitor arrangement. In this arrangement, for only three capacitors, for example, there is a choice selection of six output capacitance values for the ICD system. With four capacitors, there is a choice selection of 15 output capacitance values for the ICD system.

The present invention allows for a mode of operation of the ICD system that is not available in existing ICD systems for which the countershock energy of a particular pulse can be adjusted only by altering the initial discharge voltage or the pulse duration. By providing a capacitor system for and ICD system that has a choice of output capacitance values, in addition to having choices for the other two variables of initial discharge voltage and pulse duration, it is possible, for example, to deliver a low-energy countershock pulse (e.g., for cardioversion) having a high initial discharge voltage, while wasting only a small fraction of the energy stored initially in the capacitor system. In the prior art, one must frequently make unattractive compromises, accepting a lower voltage than desired, or wasting excessive amounts of stored energy in the capacitor system, in order to achieve lower output energy countershocks. In addition, for a given ICD system effectiveness and battery life, it is possible with the present invention to use a smaller and lower-energy battery because its energy will be used more efficiently than in the existing ICD systems which cannot vary their output capacitance.

A primary objective of the present invention is to provide an implantable cardioversion-defibrillation (ICD) system having a programmable range of output capacitance values available.

Another significant objective of the present invention is to provide an ICD system that can maintain a high and effective initial discharge voltage without wasting excessive energy, even when the energy of the countershock is substantially reduced.

A further significant objective of the present invention is to provide an ICD system with unprecedented programming flexibility for the capacitive countershock, through simultaneous manipulation of initial voltage, pulse duration, output capacitance value and waveform for each countershock in a therapy regimen.

BRIEF DESCRIPTION OF THE DRAWINGS

FIG. 1 illustrates a simplified electrical schematic diagram of a first preferred embodiment of the present invention;

FIG. 2 illustrates a simplified electrical schematic diagram of a second preferred embodiment of the present invention;

DETAILED DESCRIPTION OF THE PREFERRED EMBODIMENT

Figure 3:
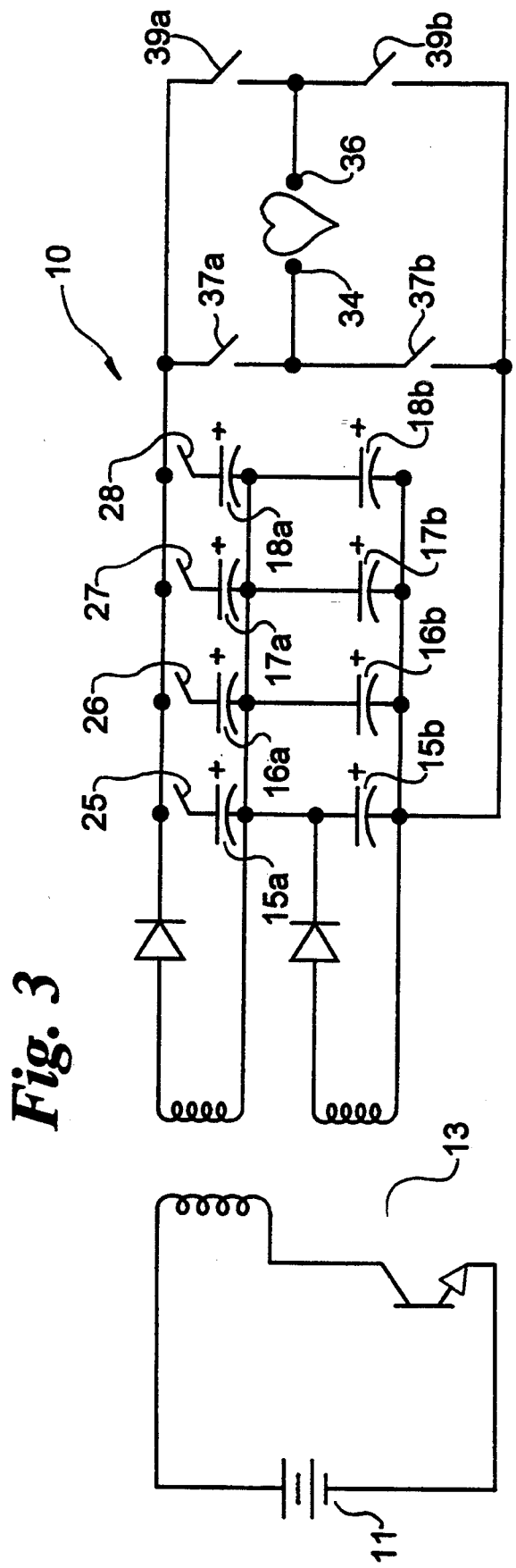
FIG. 3 illustrates a more detailed electrical schematic diagram of the first preferred embodiment of FIG. 1 including an H-bridge for producing a biphasic waveform countershock.

FIG. 1 illustrates a simplified electrical schematic diagram of the present invention of a first embodiment of an implantable cardioverter-defibrillator (ICD) system 10, including control circuitry 12 that charges in parallel any desired combination of the four capacitors 15, 16, 17 and 18 having the values given in the box 22, by manipulating the four switches 25, 26, 27 and 28 each in series with its corresponding capacitor, correspondence being indicated by means of a common digit. The switch 32 when commanded by the control circuitry 12 discharges the chosen capacitors in parallel through the cardiac electrodes 34 and 36 and into the heart tissue, this being accomplished through the conductors 42 and 44. It will be understood that the schematic diagram of FIG. 1 is simplified to highlight the novelty of the present invention and that the details and operation of the control circuitry 12 and switch 32 are known in the art.

In the embodiment shown in FIG. 1, four capacitors are used for the capacitor system with the capacitor values chosen in microfarads are 10, 20, 40, and 80. By appropriate selection among these values, only four in number, one can thus achieve any desired value of capacitance from 10 microfarads to 150 microfarads in 10-microfarad steps. The capacitor combinations needed for this purpose are as follows:

10=10
20=20
30=20+10
40=40
50=40+10
60=40+20
70=40+30
80=80
90=80+10
100=80+20
110=80+20+10
120=80+40
130=80+40+10
140=80+40+20
150=80+40+20+10

It is evident that variations on this arrangement provides one to use fewer capacitors and accept fewer steps, or to adjust the maximum capacitance to any desired value. The first embodiment of FIG. 1 provides a maximum of 150 microfarads of capacitance, although it will be recognized that a wide range of minimum and maximum effective output capacitance values can be achieved by selecting different capacitance values for each of the capacitors. The price paid for this huge increase in flexibility is a small increase in the physical volume of the capacitive components. That is, in this example, the four capacitors would have an aggregate volume slightly larger than would one 150 microfarad capacitor because of the individual encapsulations of each capacitor. The four additional switches 25, 26, 27, and 28 and the nominal additional control mechanisms for controlling and programming the switches also involves a volume increment; however, such circuitry increments involve incremental volume that is small compared to the volumes of capacitors and batteries.

FIG. 3 illustrates a more detailed schematic diagram of the first embodiment of the ICD system 10 in which each of the capacitors 15, 16, 17, and 18 is a capacitor system comprised of a pair of electrolytic capacitors, e.g., 15a and 15b, each of which is charged by a split winding transformer 13 powered by a battery source 11 which together comprise the energy-supplying portion of control circuitry 12. Switches 37a, 37b, 39a and 39b comprise a conventional H-bridge circuit operating under control of control circuitry 12 to control the polarity of the discharged countershock as received by the heart in order to generate a biphasic countershock of the preferred embodiment.

FIG. 2 illustrates an electrical schematic diagram of a second embodiment of an implantable cardioverter-defibrillator (ICD) system 10, including control circuitry 52 that charges in parallel any desired combination of the three capacitors 55, 56, and 57 having the values given in the box 62, by manipulating the three switches 65, 66 and 67, each in series with its corresponding capacitor, correspondence being indicated by means of a common digit. The switch 32 when commanded by the control circuitry 52 discharges the chosen capacitors in parallel through the cardiac electrodes 34 and 36 and into the heart tissue, this being accomplished through the conductors 42 and 44.

In the embodiment shown in FIG. 2, only three capacitors are used for the capacitor system of the ICD 10, the capacitors having the values of 20, 30 and 40 microfarads. The many variations on these examples are within the teaching and scope of the present invention. The resulting component combinations this time are these:

20=20
30=30
40=40
50=30+20
60=40+20
70=40+30
90=40+30+20

With this set of capacitance values available to the ICD programmer, and assuming a monophasic waveform with an initial voltage of 800 volts, then one can choose to store initial energies ranging from 6.4 joules to 28.8 joules. By choosing a pulse duration in each case that delivers at least 50%, and preferably 75-80% of the energy stored initially, the physician/programmer can vary the energy delivered from 5.44 joules to 24.5 joules, and the corresponding energy wasted ranges only from 0.74 joules to 4.3 joules. Throughout this full range, the initial voltage can be held at the high therapeutically effective value of 800 volts.

For the sake of comparison, let one take for a prior art example a 140-microfarad capacitor charged to an initial voltage of 750 volts. At maximum energy, this system stores 39.3 joules, delivering 34.0 joules, and wasting 5.3 joules for a pulse duration of 7 ms milliseconds with a typical 50 ohm myocardial resistance load. Assuming now that a lower energy countershock is desired from this system, the physician/programmer has two unattractive options. For clearest illustration, let one take extreme examples of delivering a cardioversion pulse of about only 5 joules. The first option would be to decrease the pulse duration and maintain the initial voltage of 750 volts; however in order to delivery only about 5 joules, the countershock would have to be truncated after about 0.48 ms. This means that the final voltage would be 700 volts and about 34.3 joules stored in the pulse-generating capacitor would be wasted. The other extreme option, of course, is to reduce initial voltage and maintain a pulse duration of 7 milliseconds, for example. In this case, the initial voltage must be dropped to about 287 volts, which is dangerously low in most circumstances. A further complication is that the final voltage becomes correspondingly low, on the order of 105 volts, and it is well-known that a low-voltage "tail" on a shock waveform can aggravate an arrhythmia rather than correcting it.

Figure 4:
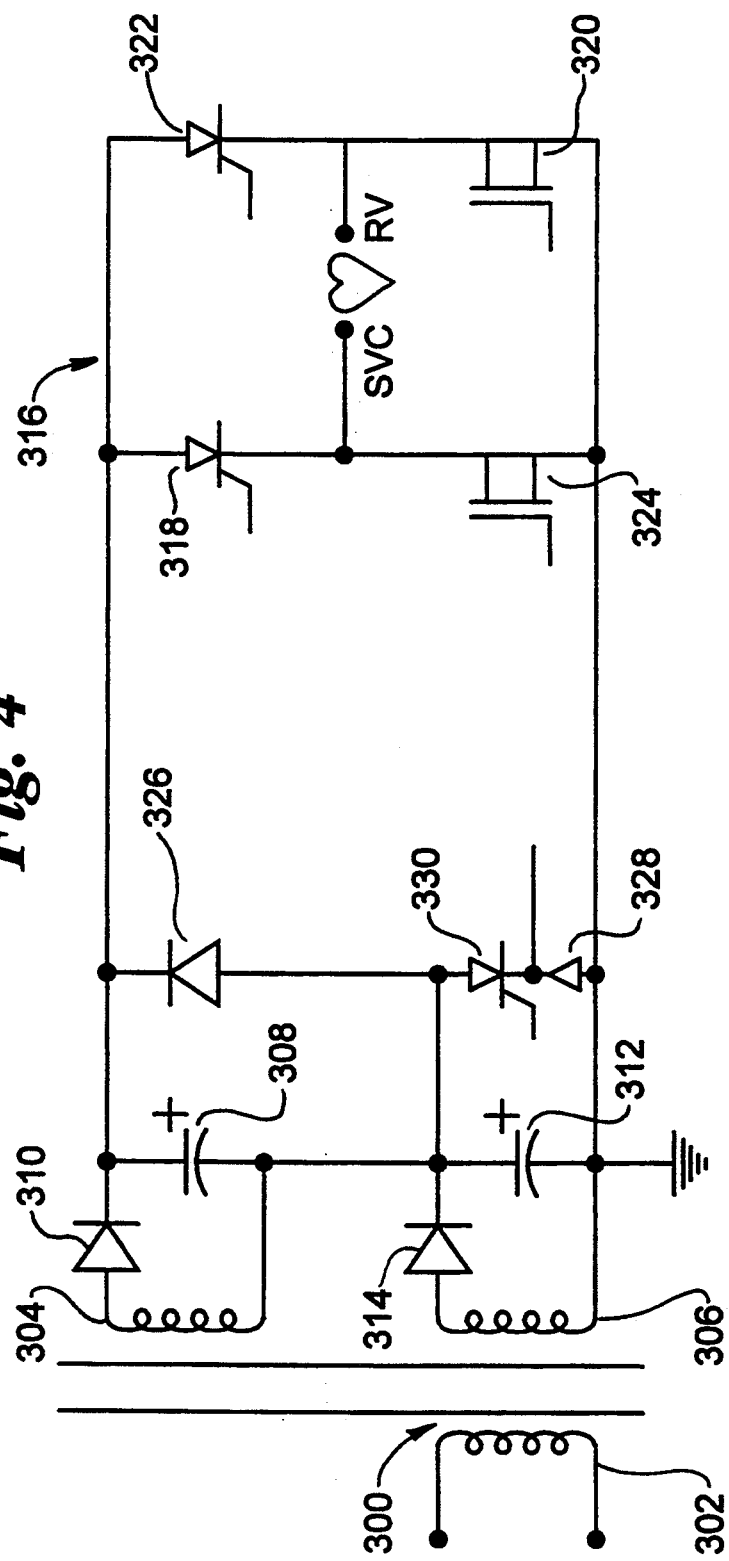
FIG. 4 illustrates a detailed electrical schematic diagram of a third preferred embodiment of the present invention.

FIG. 4 illustrates a circuit that is capable of producing a variable output capacitance waveform in which the capacitor systems may be switched from series to parallel connection to change their topology. Transformer 300 provides the power source to charge the circuit. Transformer 300 has a primary winding 302 and two secondary windings 304, 306. Secondary winding 304 charges capacitor 308 through diode 310. Secondary winding 306 charges capacitor 312 through diode 314. The H bridge circuit 316 is of conventional design.

For the positive phase of a biphasic countershock, semiconductor switches 318 and 320 are turned on. To change polarity to the negative phase of the biphasic countershock, switches 322 and 324 are turned on.

For parallel discharging of capacitors 308 and 312, capacitor 38 is discharged through diode 326 and capacitor 312 is simultaneously discharged directly through H bridge 316 and back through diode 328.

To change the topology from parallel capacitor discharge to series capacitor discharge, SCR switch 330 is turned on. This serves to discharge capacitor 312 through the negative terminal of capacitor 308, thus placing capacitors 308 and 312 in series configuration.

Figure 5:
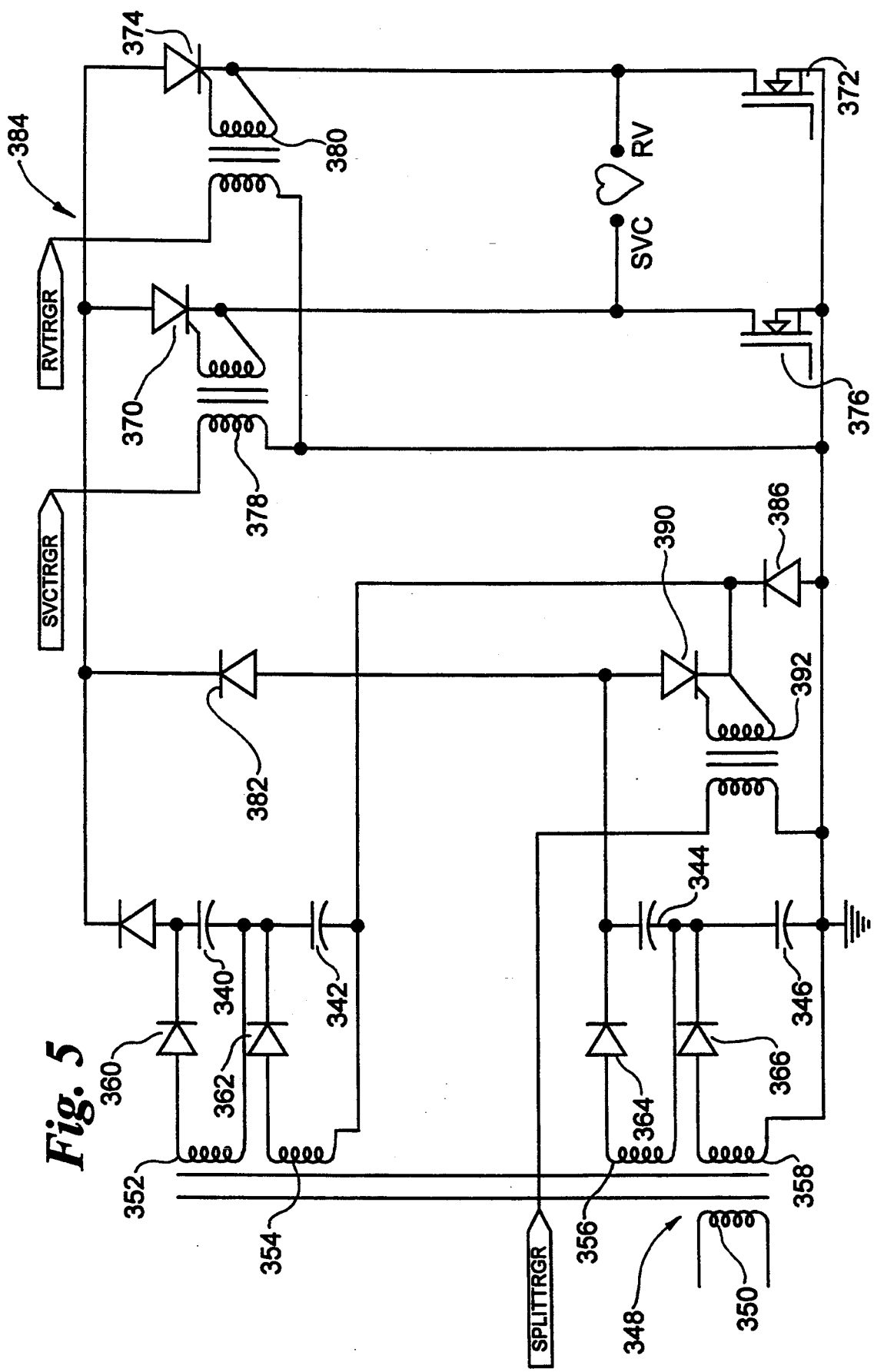
FIG. 5 illustrates a detailed electrical schematic diagram of a fourth preferred embodiment of the present invention.

FIG. 5 illustrates another alternative circuit to provide variable output capacitance values. This circuit is substantially identical in its countershock waveform to the circuit depicted in FIG. 4. At present, efficient capacitors capable of high enough voltage operation to be sufficient for defibrillation are not available with the sufficient compactness necessary for implantation in a human. Accordingly, to realize the necessary high voltage, two capacitors are utilized in series to provide the output that is desired from a single efficient capacitor, if such capacitor were available. Accordingly, the circuit of FIG. 5 includes capacitors 340, 342, 344 and 346. Each capacitor 340, 342, 344 and 346 is preferably a 60 $\mu$F, 375 volt electrolytic capacitor. Capacitors 340 and 342 are connected in series and function together as a single capacitor system having a maximum rated voltage of 750 volts and an effective capacitance of 30 $\mu$F. Capacitors 344 and 346 are also connected in series and function together as a second capacitor system having the same characteristics. The series connections just described are not affected during the topology change that is made to effect the variable output capacitance or desire waveform of the present invention The topology changes affect the relationship of the first capacitor system comprised of capacitors 340 and 342 with respect to the second capacitor system comprised of capacitors 344 and 346.

Transformer 348 has a primary winding 350 and four secondary windings 352, 354, 356 and 358. Secondary winding 352 charges capacitor 340 through diode 360. Secondary winding 354 charges capacitor 342 through diode 362. Secondary winding 356 charges capacitor 344 through diode 364. Secondary winding 358 charges capacitor 346 through diode 366

For the positive phase of a biphasic countershock, semiconductor switches 370 and 372 are turned on. To change polarity to the negative phase, switches 374 and 376 are turned on. The switching of semiconductor switch 370 is controlled by transformer 378 and the switching of semiconductor switch 374 is controlled by transformer 380.

For parallel discharging of the capacitor system made up of capacitors 340, 342 and the capacitor system made up of capacitors 344, 346, the capacitor system made up of capacitors 340, 342 is discharged though diode 382 and the capacitor unit made up of capacitors 344, 346 is simultaneously discharged through H-bridge 384 and back through diode 386.

To change the topology from parallel capacitor discharge to series capacitor discharge, semiconductor switch 390 is turned on by transformer 392. This serves to discharge the capacitor system made up of capacitors 344, 346 through the negative terminal of the capacitor system made up of capacitors 340, 342, thus placing the capacitor system made up of capacitors 340, 342 and the capacitor system made up of capacitors 344, 346 in a series configuration. Thus, the parallel topology is actually a two-by-two arrangement, where two capacitors in series are in parallel with two capacitors in series. The series topology is then four capacitors in series.

I claim:

1. An improved implantable cardioverter defibrillator system for producing a capacitive-discharge countershock, the implantable cardioverter defibrillator system being a self-contained human implantable device including a pulse-generating capacitor means for storing an electrical charge of greater than 1 joule, means for internally charging the pulse-generating capacitor means, and means for selectively discharging the electrical charge in the pulse-generating capacitor as a countershock to be delivered through electrodes adapted to be implanted in a human patient in response to a sensing of a myocardial arrhythmia in the human patient, the improvement comprising:

the pulse generating capacitor means including:
two or more separate capacitor systems; and
means for selectively electrically connecting each of the capacitor systems in parallel with the other capacitor systems during the charging and discharging of the pulse-generating capacitor means,
such that the pulse generating capacitor means has at least two
different selectable effective output capacitance values.

2. The improved system of claim 1 wherein there are three or more separate capacitor systems as part of the pulse generating capacitor means and wherein the means for selectively electrically connecting further includes a switch means for each capacitor system in series connection with an output terminal of the capacitor system for selectively determining whether the capacitor system is excluded from connecting with the other capacitor systems during the discharging of the pulse generating capacitor means.

3. The improved system of claim 1 wherein a truncated duration of the countershock and the output capacitance value of the system are always selected such that the total electrical charge delivered to the implanted electrodes exceeds about one half of the electrical charge initially stored in the pulse generating capacitor.

4. The improved system of claim 1 wherein a truncated duration of the countershock and the output capacitance value of the system are always selected such that the total electrical charge delivered to the implanted electrodes exceeds about three-quarters of the electrical charge initially stored in the pulse generating capacitor.

5. The improved system of claim 1 wherein the effective output capacitance value can be programmed when the device is implanted.

6. The improved system of claim 1 wherein each capacitor system is comprised of a pair of electrolytic capacitors connected in series and charged by a split winding transformer.

7. The improved system of claim 1 wherein the means for selectively discharging the electrical charge includes means for storing selected control information to generate a preprogrammed sequence of countershocks to be delivered as part of a multiple-countershock therapy regimen in response to a continued sensing of the myocardial arrhythmia, and wherein the selected control information includes a programmable initial charging voltage value and a programmable pulse duration value for each countershock and further includes a programmable effective output capacitance value for each countershock for controlling the means for selectively electrically connecting each of the capacitor systems.

8. The improved system of claim 7 further comprising
means for storing waveform control information as part of the control information in order to produce at least two different waveforms for the defibrillation countershocks of the therapy regimen; and,
switching means operably connected to the means for selectively discharging the electrical charge and responsive to the waveform control information for delivering as part of the therapy regimen a second of the at least two different waveforms that is different in waveform from a first of the at least two different waveforms.

9. The improved system of claim 7 wherein the at least two different waveforms are different due to different wave paths among the implanted electrodes through which the waveforms are discharged.

10. The improved system of claim 7 wherein the at least two different waveforms are different due to different wave shapes between the waveforms.

11. The improved system of claim 1 wherein the means for selectively discharging the electrical charge automatically sets the effective output capacitance value for the pulse-generating capacitor means prior to internal charging of the pulse-generating capacitor means such that an initial discharge voltage of the countershock remains substantially the same even when the pulse-generating capacitor means is charged to a stored energy value lower than a maximum stored energy value for a maximum effective output capacitance value of the pulse-generating capacitor means.

12. The improved system of claim 1 wherein the means for selectively discharging the electrical charge automatically sets the effective output capacitance value for the pulse-generating capacitor means prior to internal charging of the pulse-generating capacitor means such that a discharge duration of the countershock remains substantially the same even when the pulse-generating capacitor means is charged to a stored energy value lower than a maximum stored energy value for a maximum effective output capacitance value of the pulse-generating capacitor means.

* * * * *